(12) United States Patent
Martin et al.

(10) Patent No.: US 9,782,147 B2
(45) Date of Patent: Oct. 10, 2017

(54) APPARATUS AND METHODS FOR LOCALIZATION AND RELATIVE POSITIONING OF A SURGICAL INSTRUMENT

(71) Applicant: Analogic Corporation, Peabody, MA (US)

(72) Inventors: Robert C. G. Martin, Louisville, KY (US); Benjamin W. Neese, Washington, DC (US); Prashanth Dumpuri, Nashville, TN (US); James D. Stefansic, Nashville, TN (US)

(73) Assignee: Analogic Corporation, Peabody, MA (US)

( * ) Notice: Subject to any disclaimer, the term of this patent is extended or adjusted under 35 U.S.C. 154(b) by 370 days.

(21) Appl. No.: 13/786,677

(22) Filed: Mar. 6, 2013

(65) Prior Publication Data

US 2014/0078138 A1 Mar. 20, 2014

Related U.S. Application Data

(60) Provisional application No. 61/607,558, filed on Mar. 6, 2012.

(51) Int. Cl.
| | |
|---|---|
| *G06T 7/00* | (2017.01) |
| *G06T 17/00* | (2006.01) |
| *A61B 8/00* | (2006.01) |
| *G06T 19/00* | (2011.01) |
| *A61B 8/08* | (2006.01) |

(Continued)

(52) U.S. Cl.
CPC ............. *A61B 8/00* (2013.01); *A61B 8/0841* (2013.01); *A61B 34/20* (2016.02); *G06T 7/0012* (2013.01); *G06T 17/00* (2013.01); *G06T 19/00* (2013.01); *A61B 2034/2055* (2016.02); *A61B 2090/378* (2016.02); *G06T 2210/41* (2013.01)

(58) Field of Classification Search
None
See application file for complete search history.

(56) References Cited

U.S. PATENT DOCUMENTS

| | | | |
|---|---|---|---|
| 2003/0000535 A1* | 1/2003 | Galloway et al. | 128/898 |
| 2003/0032878 A1* | 2/2003 | Shahidi | 600/429 |

(Continued)

*Primary Examiner* — Yi Wang
(74) *Attorney, Agent, or Firm* — Anthony M. Del Zoppo, III; Driggs, Hogg, Daugherty & Del Zoppo, Co., LPA

(57) ABSTRACT

Systems, apparatus and methods for localizing and/or determining the relative position of surgical instruments during a surgical procedure are disclosed. A method includes capturing an image depicting at least a portion of a first surgical instrument disposed at a first position with respect to a target tissue, and at least a portion of a second surgical instrument disposed at a second position with respect to the target tissue, the second position different from the first position. The method includes transforming the image to a three-dimensional model so the first position of the portion of the first surgical instrument is rendered with the three-dimensional model, and the second position of the portion of the second surgical instrument is rendered with the three-dimensional model. The method includes calculating distance between the portion of the first surgical instrument and the portion of the second surgical instrument based on the three dimensional model.

19 Claims, 6 Drawing Sheets

(51) Int. Cl.
   *A61B 34/20*     (2016.01)
   *A61B 90/00*     (2016.01)

(56) References Cited

U.S. PATENT DOCUMENTS

2006/0241368 A1* 10/2006 Fichtinger .............. A61B 5/055
                                                        600/407
2009/0088634 A1*  4/2009 Zhao et al. .................. 600/427

* cited by examiner

… (1, 2)

APPARATUS AND METHODS FOR LOCALIZATION AND RELATIVE POSITIONING OF A SURGICAL INSTRUMENT

CROSS REFERENCE TO RELATED APPLICATIONS

This application claims priority to and the benefit of U.S. Patent Application No. 61/607,558 entitled "Ablation Needle Localization Using Tracked Intraoperative Ultrasound," filed Mar. 6, 2012, the disclosure of which is hereby incorporated by reference herein in its entirety.

BACKGROUND

The embodiments described herein relate to image-guided surgical techniques and more particularly apparatus and methods for localizing and/or determining the relative position of surgical instruments, such as ablation needles, during a medical procedure, such as an ablation procedure.

Image-guided therapy (IGT), which is also often referred to as image-guided intervention (IGI), has gained widespread attention and clinical acceptance for use in localizing tumors in abdominal organs. Procedures that utilize IGT include, but are not limited to, tumor biopsy, ablation, and resection. IGT describes the interactive use of medical images, often taken preoperatively, during a percutaneous medical procedure, and is often referred to as a "global positioning system" (GPS) for interventional radiology. By way of analogy, in an automobile GPS, the current position of a vehicle is accurately localized or "registered" onto an electronic roadmap that is updated as the automobile moves. The driver can use the GPS as a guide to see where their vehicle is, where it has been, where it is headed, and a planned route with which to follow to arrive at a selected destination. IGT allows a physician to accomplish essentially the same thing with one or more tracked medical instruments on a three-dimensional (3D) "roadmap" of highly detailed tomographic medical images of the patient that are acquired during and/or before the interventional procedure. Often, the key to an IGT procedure is the accurate registration between real "patient" space (e.g., during a procedure) and medical image space (e.g., preoperatively collected), such that an accurate absolute or relative position of a surgical instrument can be accurately determined.

In some IGT procedures, a 3D map or plan is developed using preoperative diagnostic images, possibly days before the actual procedure and in consultation with a variety of physicians in different disciplines. On the day of the IGT procedure, the position of the patient and the medical instruments are accurately localized or "registered" onto the preoperative images. As the physician moves the instrument, the precise location of its tip is updated on the 3D images. The exact location of the instrument is confirmed with a form of real-time imaging, including, but not limited to, intraoperative computed tomography (CT), two-dimensional (2D) fluoroscopy, or ultrasonic (US) imaging.

One type of IGT procedure includes Irreversible Electroporation (IRE), in which one or more ablation needles can be positioned within the patient. The ablation needles have to be positioned accurately within the patient's anatomy. Additionally, when more than one needle is used for treatment, relative distances between the needles determine the efficacy of the treatment. In IRE procedures, relative needle distances determine the size of an irreversible electroporation zone, and therefore the volume of tissue/tumor that is destroyed. Some surgeons rely on two dimensional (2D) ultrasound images to localize the position of the ablation needles and to determine the relative distances between the needles. An example of such a technique is disclosed in PCT Publication No. WO 2004/019799, entitled "Methods and systems for localizing of a medical imaging probe and for spatial registration and mapping of a biopsy needle during a tissue biopsy," which is hereby incorporated by reference herein in its entirety. The lack of dimensionality in 2D ultrasound, however, renders known methods unable to localize more than one needle in a single ultrasound image.

Thus, a need exists for systems, apparatus and methods for localizing and/or determining the relative position of surgical instruments, generally, and of ablation needles in particular, for example, in a three-dimensional space and/or with respect to multiple instruments. A need also exists for a system, apparatus and method for localizing and/or determining when accounting for a relationship between a patient's pre-operative diagnostic images and the physical space in which the ultrasound images are captured.

SUMMARY

Systems, apparatus and methods for localizing and/or determining the relative position of surgical instruments, such as ablation needles, during a surgical procedure are disclosed herein. In some embodiments, a method includes capturing an image depicting at least a portion of a first surgical instrument disposed at a first position with respect to a target tissue of a patient, and at least a portion of a second surgical instrument disposed at a second position with respect to the target tissue of the patient, the second position different from the first position. The method also includes transforming the image to a three-dimensional model such that (1) the first position of the portion of the first surgical instrument is rendered with the three-dimensional model, and (2) the second position of the portion of the second surgical instrument is rendered with the three-dimensional model. The method further includes calculating a distance between the portion of the first surgical instrument and the portion of the second surgical instrument based on the three dimensional model.

DETAILED DESCRIPTION

Figure 1:
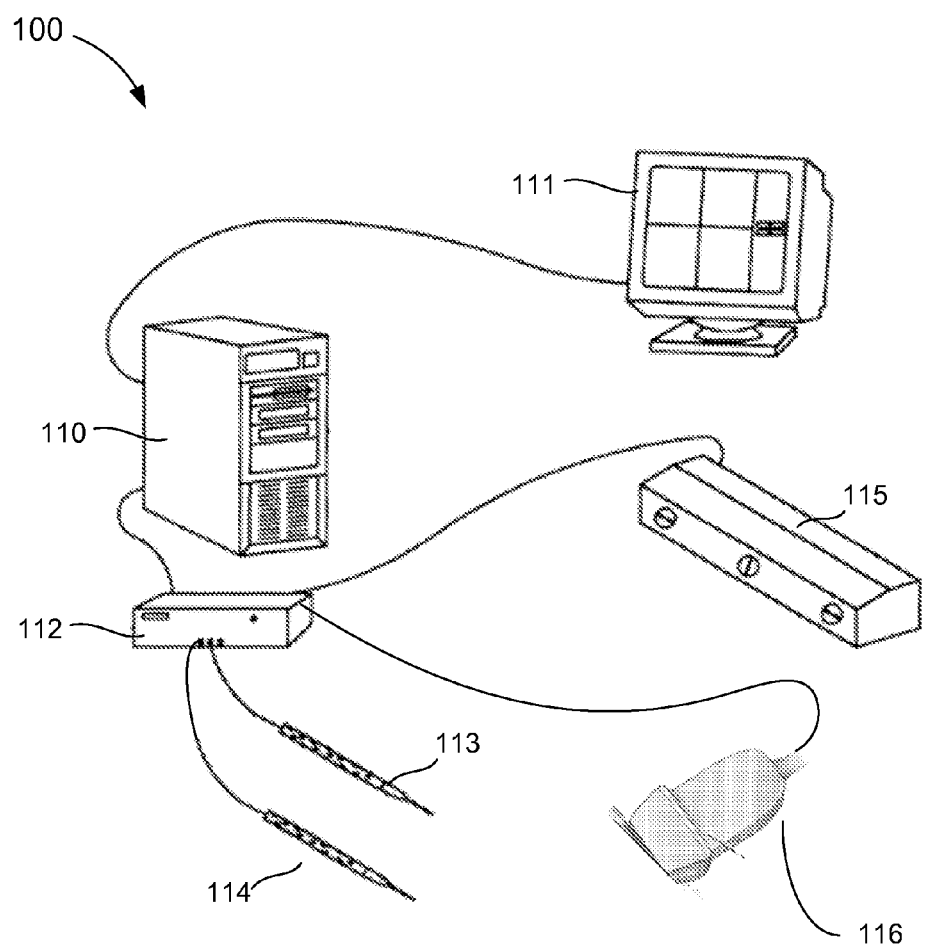
FIG. 1 is a schematic illustration of a system for calculating the relative distances of surgical instruments, according to an embodiment.

Systems, apparatus and methods for accurate absolute and relative positioning of surgical instruments, such as ablation needles, during a medical procedure, are described herein. The position of the surgical instruments can be determined using image-guided surgical techniques. The goal of image-guided surgery (IGS) is to allow the clinician to interactively use high resolution, high contrast pre-procedural tomographic image data during the intervention via an overlay display of tracked surgical instrumentation.

Prior to an interventional procedure, at least a portion of a patient can be scanned with an imaging device of a system. Images produced by the imaging device can be used by the system to produce a three-dimensional (3D) model of the patient or a portion of the patient, such as a target tissue. The target tissue can include any suitable bodily tissue, such as, for example, an organ and/or tissue adjacent to the organ. For example, diagnostic imaging of the patient can utilize x-ray, magnetic resonance imaging (MRI), ultrasound (US), and/or any other suitable imaging technology. Any suitable number of diagnostic images can be taken and used to create the 3D model for example, using computed tomography (CT). In this manner, the 3D model includes pre-procedural tomographic image data.

A registration scan can be performed shortly before or during the procedure, such as when the patient is in the operating room. The registration scan can produce at least one 2D image. The 2D image produced by the registration scan can be used to register the physical space, which can include the physical space surrounding and/or including the patient, such as, for example, at least a portion of the operating room and/or at least a portion of the patient. More specifically, the 2D image produced by the registration scan can be used to register the physical space to the 3D model. Registration is a method of determining the mathematical relationship between two coordinate spaces, such as the physical space and the model space. Registration can be affected by acquiring surface data using laser range scanning (LRS) technology, manually with an optically or electromagnetically tracked stylus or ablation instrument, or via any other collection modality. In some embodiments, a system can be used to compute the mathematical transformation that allows for the display of the location of tracked instrumentation on the pre-procedural tomographic image data.

IGS can be used to map the location of tracked percutaneous ablation instrumentation onto the pre-procedural tomographic data. For example, the system can be used to track, localize, and/or compute the distance between multiple monopolar electroporation probes. Moreover, the devices and methods described herein can provide accurate registration in a relatively short amount of time to display the trajectory and device locations relative to targets planned prior to surgery. In particular, pre-procedural image data can be used for guidance, which allows for pre-procedural planning (e.g., of a targeted approach for insertion of the instrumentation) and 3D model generation. Such pre-procedural image data can also be used in conjunction with registration to aid in a determination of instrument position during the procedure (i.e., an intra-procedural determination). For example, the instrument's position can be detected intra-procedurally and transformed onto pre-procedural image data.

For example, in some embodiments two instruments, such as monopolar ablation needles, can be inserted into the patient. A tip, shaft, and/or any other portion of the instruments can be tracked and transformed to the 3D model. In some embodiments, for example, the tip of each instrument can be captured in one or more 2D ultrasound images. The 2D ultrasound image can be transformed to the 3D model, and an absolute position and relative position of each instrument can be displayed on the model. A distance between the tip of each instrument can be calculated in 3D space using the model.

In some embodiments, in which more than one instrument is present, it may be difficult and/or impossible to capture an image of the tip and/or the shaft of all instruments in a single 2D image. Thus, in some embodiments, any suitable number of images can be taken. For example, at least one 2D image can be taken for each instrument. Each image can be transformed to the 3D model, allowing the position of the instrument tips (e.g., relative to the patient's anatomy and/or to another instrument, also referred to herein as the "relative position") and/or a trajectory of each instrument to be calculated. In this way, the relative position of the instrument tips can be calculated, even where all the instrument tips are not captured in a single image and/or where the instrument is flexible, which could otherwise render external instrument tracking inaccurate.

FIG. 1 is a schematic illustration of a system 100 for calculating a relative distance between surgical instruments according to an embodiment. More particularly, the system 100 can be used in conjunction with preoperative images from an imaging process (e.g., a computed tomography (CT) scan, 2D fluoroscopy, ultrasonic (US) imaging, and/or magnetic resonance imaging (MRI), not shown in FIG. 1) to perform an image-guided interventional procedure such as a biopsy, ablation, resection, or the like. The system 100 includes at least an electronic processing device 110, a display 111, a controller 112, two ablation instruments 113, 114, an optical tracking system 115, and an ultrasound device 116.

The electronic processing device 110 can be, for example, a personal computer, or the like. The electronic processing device 110 includes at least a processor and a memory. The memory (not shown in FIG. 1) can be, for example, a random access memory (RAM), a memory buffer, a hard drive, a read-only memory (ROM), an erasable programmable read-only memory (EPROM), and/or so forth. In some embodiments, the memory of the electronic processing device 110 stores instructions to cause the processor to execute modules, processes, and/or functions associated with using a personal computer application, controlling one or more medical instruments, displaying and updating a medical image, and/or the like.

The processor (not shown in FIG. 1) of the electronic processing device 110 can be any suitable processing device configured to run and/or execute a set of instructions or code. For example, the processor can be a general purpose processor, a central processing unit (CPU), an accelerated processing unit (APU), or the like. In some embodiments, the processor of the electronic processing device 110 can be included in, for example, an application specific integrated circuit (ASIC). The processor can be configured to run and/or execute a set of instructions or code stored in the memory associated with using a personal computer application, a mobile application, an internet web browser, telephonic or cellular communication, and/or the like. More specifically, in some instances, the processor can execute a set of instructions or code stored in the memory associated with transforming 2D images, e.g., images that display one or more surgical instruments, onto a 3D model.

The display 111 is configured to be in electronic communication with the electronic processing device 110. The display 111 can be any suitable display configured to provide a user interface to the electronic processing device 110. For example, the display 111 can be a cathode ray tube (CRT) monitor, a liquid crystal display (LCD) monitor, a light emitting diode (LED) monitor, and/or the like. The display 111 can be configured to provide the user interface for a personal computer application or the like. For example, the display 111 can be configured to graphically represent a medical image of an anatomical structure. In some embodiments, the display 111 can graphically represent the position of one or more medical instruments (e.g., a probing instrument, the ablation instruments 113, 114, and/or any other suitable device) as the medical instrument positioned with respect to a target tissue (e.g., an organ) of a patient and relative to a preoperative image of the target tissue. In some embodiments, the processing device 110 can be configured to map the ablation instrument 113, 114 relative to a preoperative image of the target tissue, and the display 111 can graphically represent a virtual position of the medical instrument relative to the image of the target tissue. The processing device 110 can determine the position of the ablation instruments 113 and 114 with respect to the target tissue, and, in some embodiments, can calculate a relative distance between a portion (e.g., a tip, a shaft, or the like) of each of the ablation instruments 113, 114.

As shown in FIG. 1, the electronic processing device 110 is configured to be in electronic communication with the controller 112 (e.g., via an Ethernet cable, universal serial bus (USB), SATA cable, eSATA cable, or the like). The controller 112 can be any suitable device for controlling at least a portion of the system 100. More specifically, the controller 112 can provide a user interface that can be manipulated by a user (e.g., a clinician, technician, doctor, physician, nurse, etc.) to control, for example, the ablation instruments 113, 114, the optical tracking system 115, and/or the ultrasound device 116.

The optical tracking system 115 can include, for example, an infrared tracking device. In some embodiments, the optical tracking system 115 can include any number of cylindrical lenses (e.g., three lenses) that can receive light from sequentially strobed infrared light emitting diodes (IREDs). In this manner, the optical tracking system 115 can triangulate to find each IRED relative to the position of the optical tracking system 115. In other embodiments, the optical tracking system 115 can be configured to detect a measure of reflected or refracted light. For example, in some embodiments, the optical tracking system 115 can broadcast an infrared light and can include one or more lenses configured to receive a portion of the infrared light that is reflected and/or refracted by a surface of the ablation instruments 113 and 114, the ultrasound device 116, and/or an anatomical structure.

The ultrasound device 116 can be operable to capture 2D ultrasound images of the patient pre-operatively and/or intra-operatively. For example, the ultrasound device 116 can be configured to capture one or more images of one or more salient anatomical features of the patient. The processing device 110 can register the ultrasound images to the 3D model. In some embodiments, the ultrasound device 116 can image the ablation instruments 113 and/or 114 intra-operatively, which can provide data to the processing device 110 sufficient for the processing device to transform the location or position of the ablation instruments 113 and/or 114 in the physical space to the 3D model.

Each ablation instrument 113, 114 can be any suitable instrument. For example, in some embodiments, the ablation instrument 113, 114 can include an ablation tip that can be used to microwave or heat-kill lesions and/or affect IRE. In some embodiments, each ablation instrument 113 and/or 114 can include any suitable number of IREDs configured to be tracked by the optical tracking system 115. In this manner, the IREDs can be used to define registration points that are used to map the position of the ablation instrument 113, 114 in physical space onto the preoperative image. Similarly, a portion of the ablation instrument 113,114 (e.g., a shaft, a tip, or another portion of the instrument) can be detected by the ultrasound device 116.

More specifically, when a given number of IREDs are detected by the lenses of the optical tracking system 115 and/or a probe of the ultrasound device 116, the tip and/or trajectory of each ablation instrument 113 and/or 114 can be accurately transformed from physical space to a 3D model space (e.g., by the electronic processing device 110) without placing constraints on how the ablation instruments 113 and/or 114 are handled by a surgeon. In other words, the ablation instruments 113, 114 can be moved, by the surgeon, at any speed and/or direction during a procedure without restriction from the optical tracking system 115 and/or the ultrasound device 116.

In some embodiments, at least one of the ablation instruments 113, 114 and/or the ultrasound device 116 can have twenty-four IREDs positioned in a spiral around a handle of the instrument or device. In such embodiments, the ablation instrument 113, 114 and/or the ultrasound device 116 can be sufficiently light in weight to be easily directed or otherwise maneuvered by the surgeon. In other embodiments, the ablation instrument 113, 114 and/or the ultrasound device 116 can be formed from a material and/or include a surface that is configured to reflect a portion of light. For example, in some embodiments, the ablation instrument 113, 114 and/or the ultrasound device 116 can reflect a portion of light broadcasted by the optical tracking system 115. In such embodiments, the optical tracking system 115 can receive at least a portion of the reflected light to determine the location of the ablation instrument 113, 114 and/or the ultrasound device 116. Thus, in such embodiments, the ablation instrument 113, 114 and/or the ultrasound device 116 need not include IREDs.

In some embodiments, the position of the ablation instrument 113, 114 can be determined with a tip location error of 0.35 mm in 3D space. In other words, the location of the tip of the ablation instrument 113, 114, as detected by the optical tracking system 115 for example, is within a margin of error of 0.35 mm of the actual location of the tip of the ablation instrument 113, 114 in the physical space represented by the space in the 3D image. In some embodiments, a distance between the first ablation instrument 113 and the second ablation instrument 114 based on the 3D space can be slightly different then the distance measure between the instruments 113, 114 in the 2D ultrasound image. For example, a distance in the 2D image can be 1.9 cm and a distance in the 3D space can be 1.8 cm, resulting in an "error" or difference in distance measurement of 0.1 cm. In another example, a distance between the instruments 113, 114 in the 2D image can be 1.3 cm and a distance in the 3D space can be 1.6 cm, resulting in a difference in distance measurement of 0.3 cm.

In some embodiments, the processing device 110 can define a coordinate system associated with the physical space and can be configured to preserve the registration if the patient is moved. For example, in some embodiments, the system 100 can include a reference emitter (not shown) and the optical tracking system 115 can be configured to localize the ablation instrument 113, 114 and/or the ultrasound device 116 and the reference emitter in the coordinate system defined by the reference emitter. By mapping the position of the ablation instrument 113, 114 and/or the ultrasound device 116 into the space defined by the position and orientation of the reference emitter, the location of the optical tracking system 115 and/or ultrasound device 116 need not be identified during a registration (e.g., a mapping) process. Thus, the optical tracking system 115 and/or the ultrasound device 116 can be flexibly placed before surgery (i.e., the pre-surgical position of the optical tracking system 115 or ultrasound device 116 with respect to the patient is not fixed, and can be any suitable position) and can be moved or otherwise relocated during the procedure to accommodate any surgical requirements.

Figure 2:
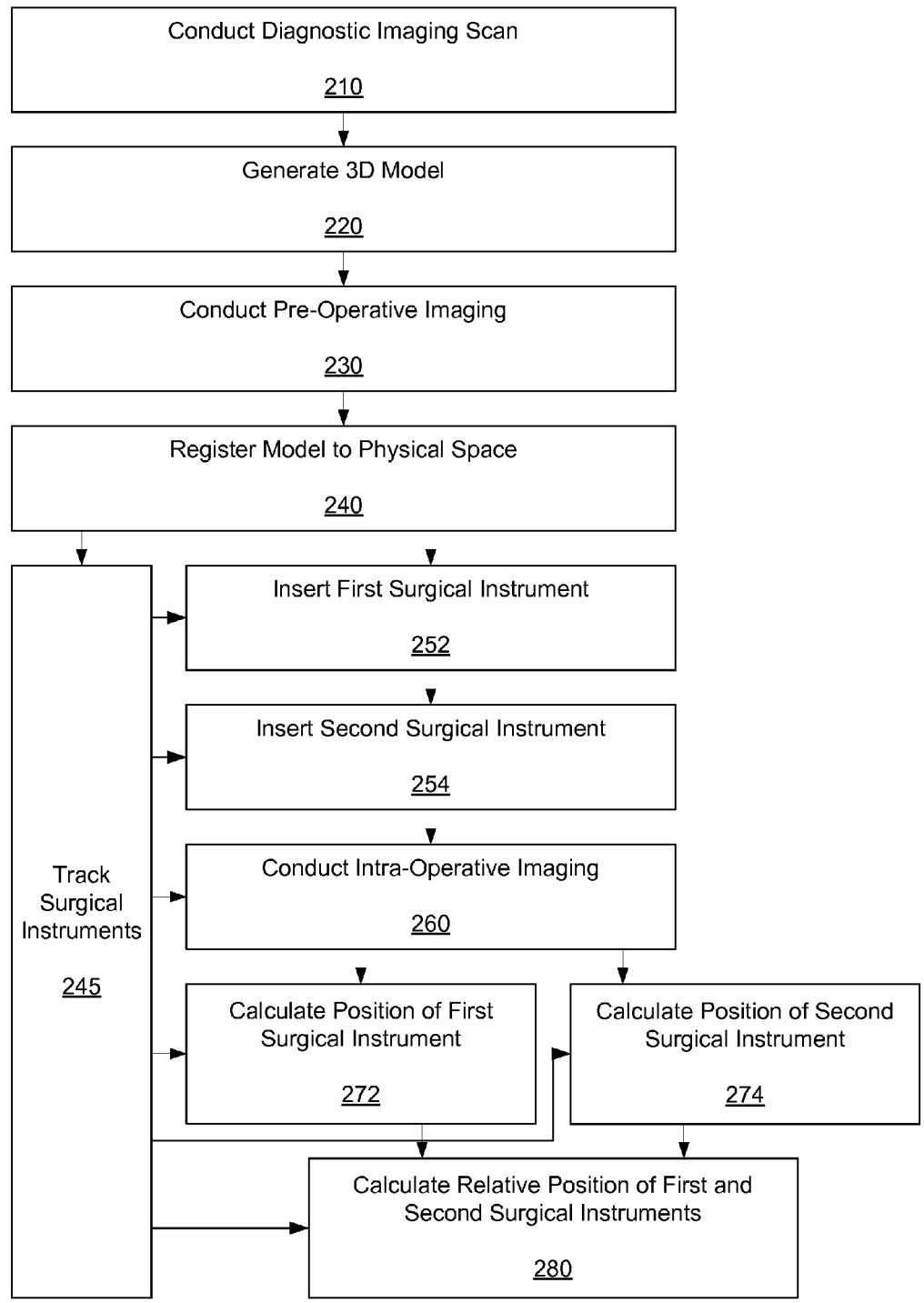
FIG. 2 is a flowchart illustrating a method of localizing surgical instruments, according to an embodiment.

FIG. 2 is a flowchart illustrating a method of localizing surgical instruments according to an embodiment. In some embodiments, the method can be used to transform the location of one or more surgical instruments (such as the ablation instruments 113, 114 described above with reference to FIG. 1) in a physical space (intra-operatively) to a model of a portion of patient anatomy rendered from images of the patient anatomy obtained pre-operatively. Thus, the transformation of the surgical instruments in physical space onto the 3D model can facilitate determining an absolute position of the surgical instruments (e.g., with respect to the patient and/or a feature of patient anatomy, such as a tumor) and/or the relative position of a first surgical instrument (e.g., ablation instrument 113) with respect to a second surgical instrument (e.g., ablation instrument 114) (such as, for example, a distance between a predetermined portion of each instrument 113, 114).

The method includes conducting a diagnostic scan of a bodily tissue of a patient with an imaging device, prior to an interventional procedure, to produce one or more images of a portion of the patient's anatomy, at 210. The portion of the patient's anatomy can include a target tissue, such as an organ. For example, in some instances, a portion of the patient can be medically imaged using X-ray, MRI, ultrasound, any other suitable imaging technology, or a combination of the foregoing. A 3D model of the patient's anatomy can be generated, at 220, from the images optioned during the diagnostic scan using, for example CT and/or other modeling techniques. For example, two, three, four or more 2D images can be taken during the diagnostic scan, at 210, and the 3D model can be generated, rendered, or otherwise produced or assembled, therefrom.

In some embodiments, the diagnostic scan, at 210, and/or the generation of the 3D model, at 220, can occur in advance of (e.g., one or more hours or one or more days prior to) a surgical intervention. For example, the diagnostic scan, at 210 and/or the generation of the 3D model, at 220, can be performed in preparation for a surgical intervention, and can be used to familiarize the surgeon with the patient's anatomy and/or condition. In some embodiments, treatment decisions, such as whether to conduct a surgical intervention, can be based on the diagnostic scan, at 210, and/or the 3D model. In some embodiments, an anatomical feature of interest, such as a tumor, lesion, cyst, and/or any other type of feature, which may be the subject of surgical intervention can be identified using the 3D model. In other embodiments, the diagnostic scan, at 210, and/or the model generation, at 220, can occur immediately before and/or during a surgical intervention. For example, the scan, at 210, and or the model generation at 220, can occur simultaneously with, or otherwise overlapping in time with, a surgical intervention. In this manner, the diagnostic scan and/or 3D model can be updated in real time (e.g., "live") or close to real time as the surgical intervention progresses.

In some embodiments, such as in embodiments in which the 3D model is not updated in real time, the physical space (e.g., the operating room and/or the patient) can be registered to the 3D model, at 240, by conducting a pre-operative registration imaging, at 230. For example, at 230, an ultrasound and/or other medical image can be captured and used to register the patient, an ultrasound device, one or more surgical instruments (e.g., ablation probes), and/or an optical tracking detector to the 3D model. Once the physical space has been registered to the model, at 240, the model can be operable to track the motion of a surgical instrument in the physical space, at 245 (e.g., using the optical tracking system 115 and/or ultrasound device 116, as described above with reference to FIG. 1).

A first surgical instrument can be inserted into the patient, at 252, and a second surgical instrument can be inserted into the patient, at 254. The surgical instruments can be tracked, at 245, based on, for example, optical tracking, for example, using optical tracking system 115 in conjunction with IREDs, as described above with reference to FIG. 1. In some embodiments, optical tracking alone may be insufficient to accurately locate the tip and/or trajectory of the instruments. For example, because some instruments, such as ablation needles may be flexible, and/or because a portion of the instrument, (e.g., the tip) may not be visible to an optical tracking system, in some embodiments, intra-operative imaging can be conducted, at 260. Intra-operative imaging, using an imaging technique such as ultrasound, X-ray, MRI, or another suitable imaging technique, can be operable to produce a 2D and/or 3D image, which can include a representation of one or more of the surgical instruments. The images returned by the intra-operative imaging can be transformed to the 3D model. Similarly stated, the 3D model generated, at 220, can be updated based on the intra-operative imaging, at 260. For example, an electronic processing device (e.g., the electronic processing device 110 as shown and described above with reference to FIG. 1) can map the intra-operative images onto the 3D model, for example, based on optical tracking of an imaging probe and/or salient anatomical features contained within the image.

The intra-operative images obtained, at 260, can include a representation of at least a portion of the surgical instruments. Thus, a position of the first surgical instrument can be calculated, at 272, and a position of the second surgical instrument can be calculated, at 274. At 280, a relative position of the first surgical instrument and the second surgical instrument with respect to each other can be calculated. For example, the model can display a distance between the first surgical implement and the second surgical implement. In some embodiments, the model can also display the position of at least one of the surgical instruments relative to the model. In this way, the surgeon can determine whether the surgical instruments are properly positioned relative to the organ or tissue to be treated and/or whether the surgical instruments are properly positioned relative to each other (e.g., whether the distance between the instruments is appropriate).

Figure 3:
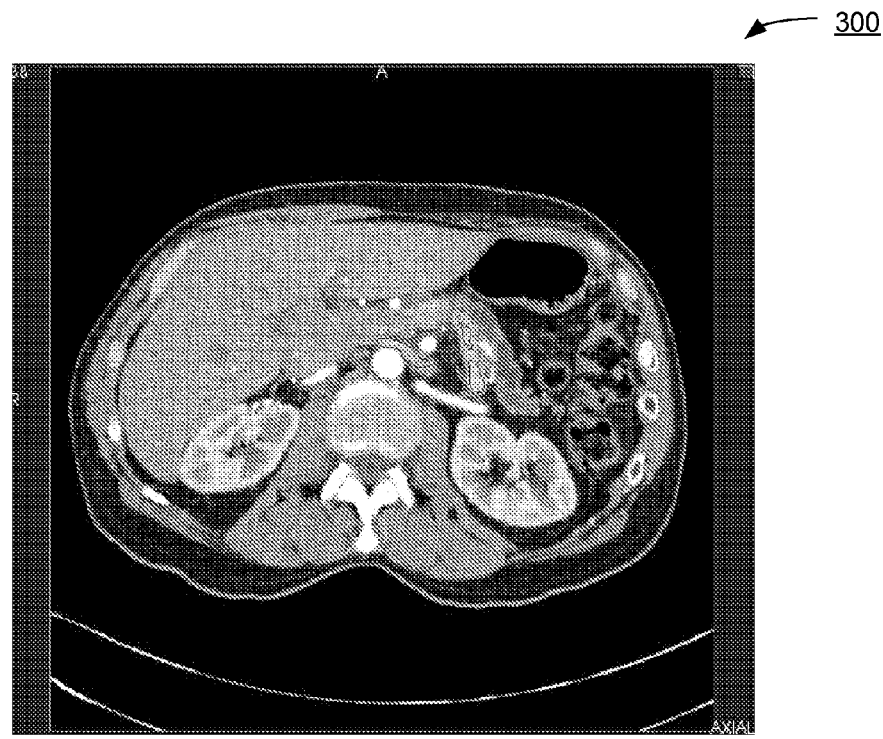
FIGS. 3 and 4 are a diagnostic image and a three-dimensional model of a pancreas, respectively.
Figure 4:
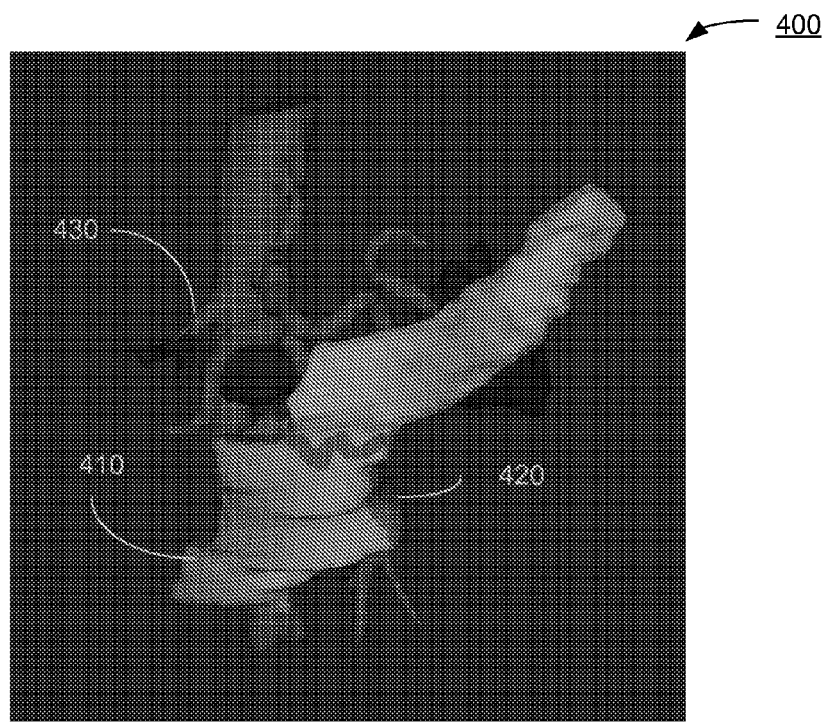

FIG. 3 is an axial diagnostic 2D X-ray image 300 of a portion of a patient's anatomy, and FIG. 4 illustrates a 3D model 400 of the portion of the patient's anatomy generated from the diagnostic X-ray image 300. The diagnostic X-ray image 300 is one of a number of X-ray images used to generate the model 400. The model 400 depicts a pancreas 410, a tumor 420, and important vasculature 430 associated with the pancreas 410. The tumor 420 would be difficult to treat using traditional surgical interventions because of its proximity to the vasculature. Some embodiments described herein, however, can enable accurate placement of multiple monopolar electroporation probes suitable for treatment of the tumor 420.

Figure 5:
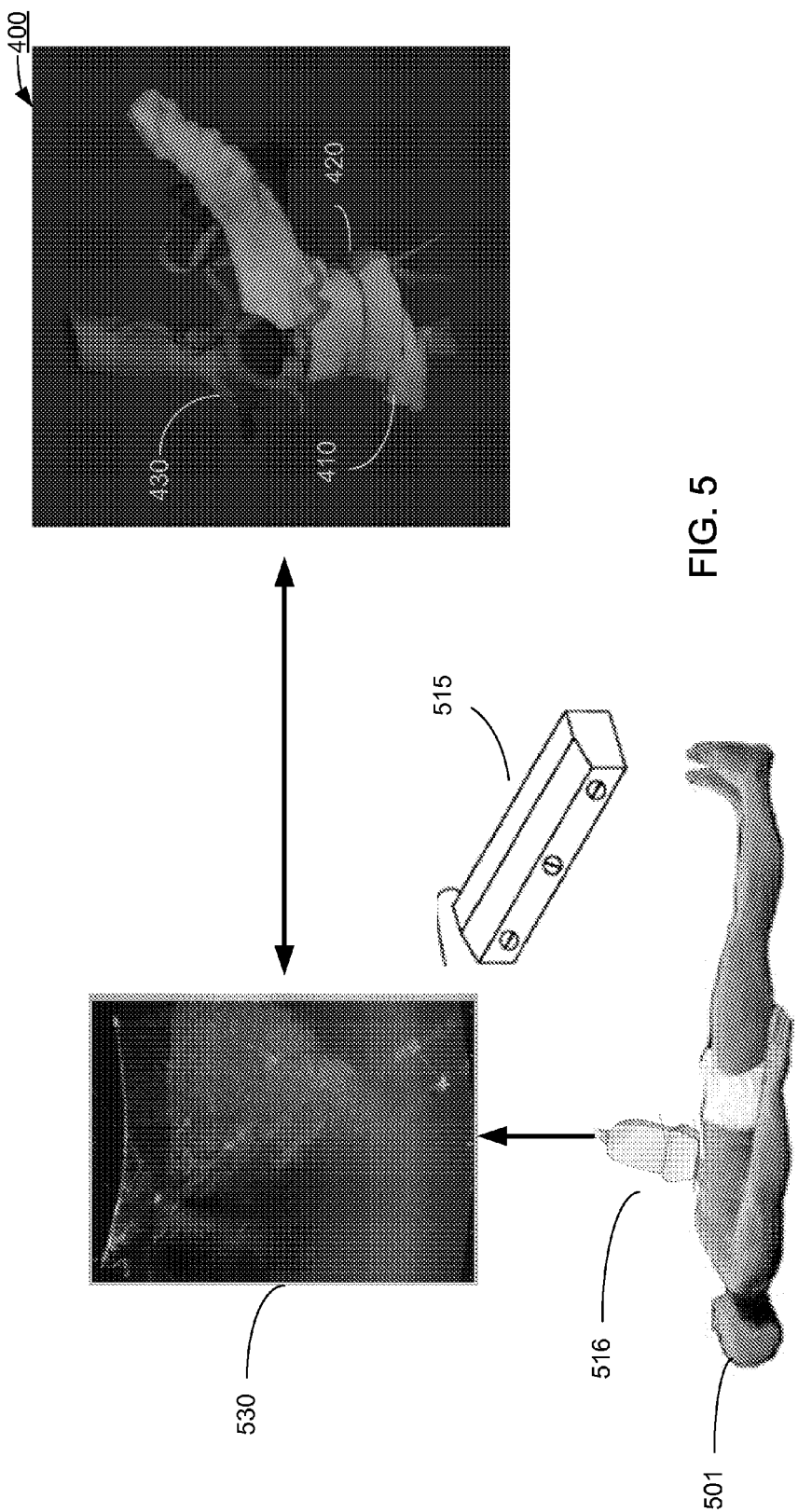
FIG. 5 is a schematic illustration of registering a physical space to a model, according to an embodiment.

FIG. 5 is a schematic illustration of registering a physical space, including a patient, with the 3D model 400. As described above with reference to FIG. 2, a physical space can be registered to a model, at 240. For example, referring to FIG. 5, a location of an ultrasound device 516 can be determined in a physical space (e.g., in the operating room) by an optical tracking system 515. The ultrasound device 516 can produce an ultrasound image 530. Having determined the location of the ultrasound device 516 in the physical space, the location of the patient's pancreas within the physical space can be determined via the ultrasound image 530. The physical space can be registered to the model 400, by detecting and/or identifying a "salient anatomical feature" (e.g., an anatomical region that can be easily identified on the surfaces of the diagnostic images and the anatomical surfaces) in the ultrasound image 530, which can be correlated with and/or transformed onto the model 400 as described in U.S. Pat. No. 8,358,818, entitled Apparatus and Methods of Compensating for Organ Deformation, Registration of Internal Structures to Images and Applications of Same," incorporated herein by reference herein in its entirety. In some embodiments, the physical space can be registered to the model 400 by detecting and/or identifying a pseudo-feature as described in U.S. Patent Application Publication No. 2011/0274324, entitled "System and Method for Abdominal surface Matching Using Pseudo-Features," incorporated herein by reference herein in its entirety.

Figure 6:
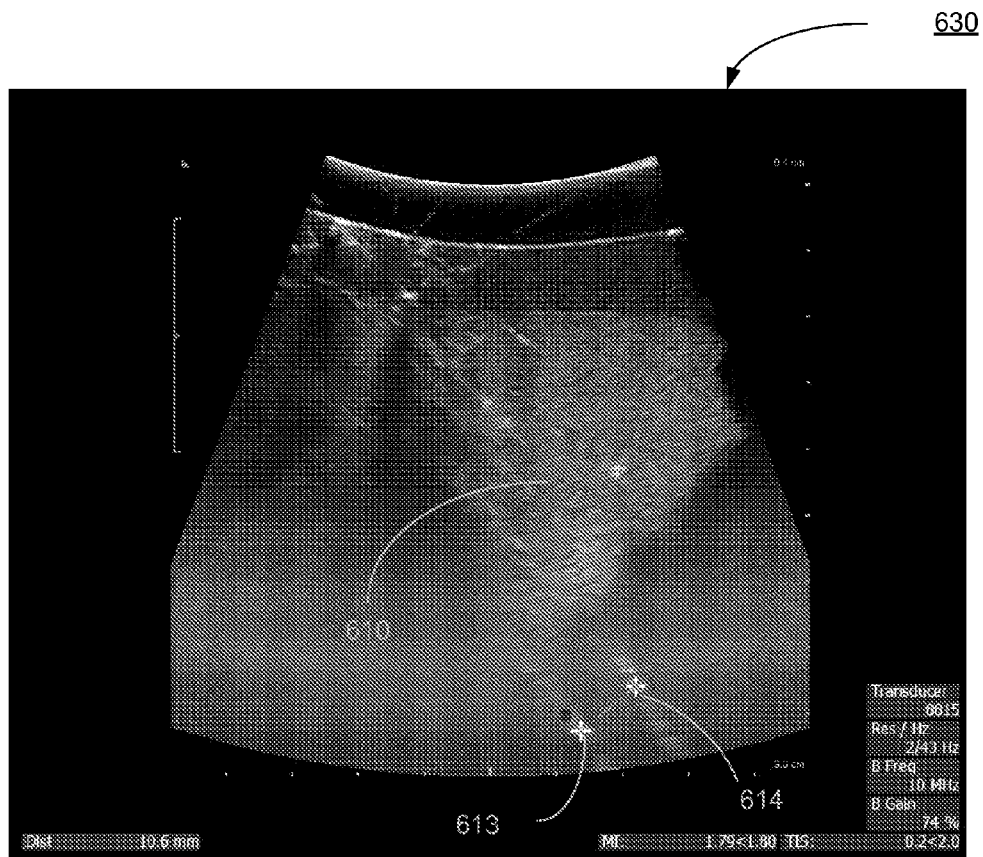
FIGS. 6 and 7 are an intra-operative ultrasound image and a three dimensional model of a liver, respectively.
Figure 7:
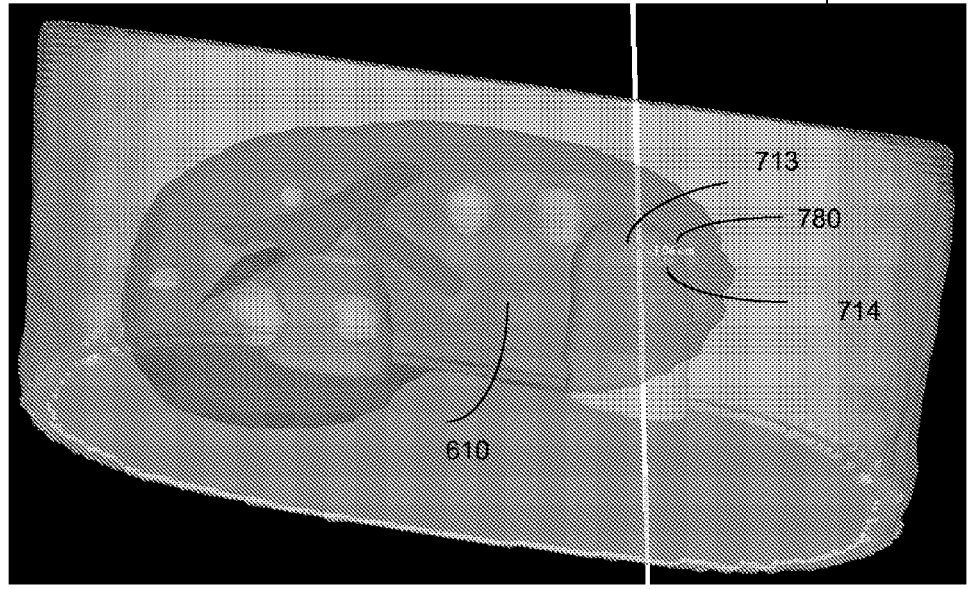

FIG. 6 depicts a 2D intra-operative ultrasound image 630 of a liver 610 of a patient, according to an embodiment. FIG. 7 depicts a 3D model 700 of the liver 610, according to an embodiment. As shown in FIG. 6, a first surgical instrument 613 and a second surgical instrument 614 are each at least partially disposed within the patient. The ultrasound image 630 can be registered to the 3D model 700, as described herein, such that the instruments 613, 614 can be transformed onto the model 700. As shown in FIG. 7, a rendering of the first instrument 713 and a rendering of the second instrument 714 are included in the 3D model 700. In this manner, a processing system (not shown in FIG. 7) can use the model 700 to calculate a distance, in the 3D model space, between the first instrument 713 and the second instrument 714. The rendering of the first instrument 713 and/or the rendering of the second instrument 714 can aid the surgeon in determining a trajectory and/or position, e.g., relative to vasculature and/or malignant tissue, of the first instrument 713 and/or the second instrument 714. For example, a tip of the instrument 713, 714 and/or one or more points along the shaft of the instrument 713, 714 can be transformed to the model 700, such that the model 700 can depict the path of each instrument 713,714 along its length.

Because the ultrasound image 630 includes the first instrument 613 and the second instrument 614, the ultrasound device (not shown in FIG. 6) used to capture the ultrasound image 630 can be operable to calculate a distance 680 between the first instrument 613 and the second instrument 614. The ultrasound distance 680 is a 2D distance calculation and reflects the distance between the first instrument 613 and the second instrument 614 in the plane of the 2D ultrasound image 630. In some embodiments, such as embodiments in which the first instrument 613 and the second instrument 614 are not co-planar with the ultrasound image 630, the 2D ultrasound distance 680 may be inaccurate. Similarly stated, in an embodiment where a distance vector defined by the tip of the first instrument 713 and the tip of the second instrument 714 has a component that is not coplanar with the ultrasound image, the 2D ultrasound distance 680 may be inaccurate. In some embodiments, such as if the ultrasound device can only capture one instrument at a time in a single image, it may not be possible to calculate a distance between the first instrument 613 and the second instrument 614 using the ultrasound image 630.

Figure 8:
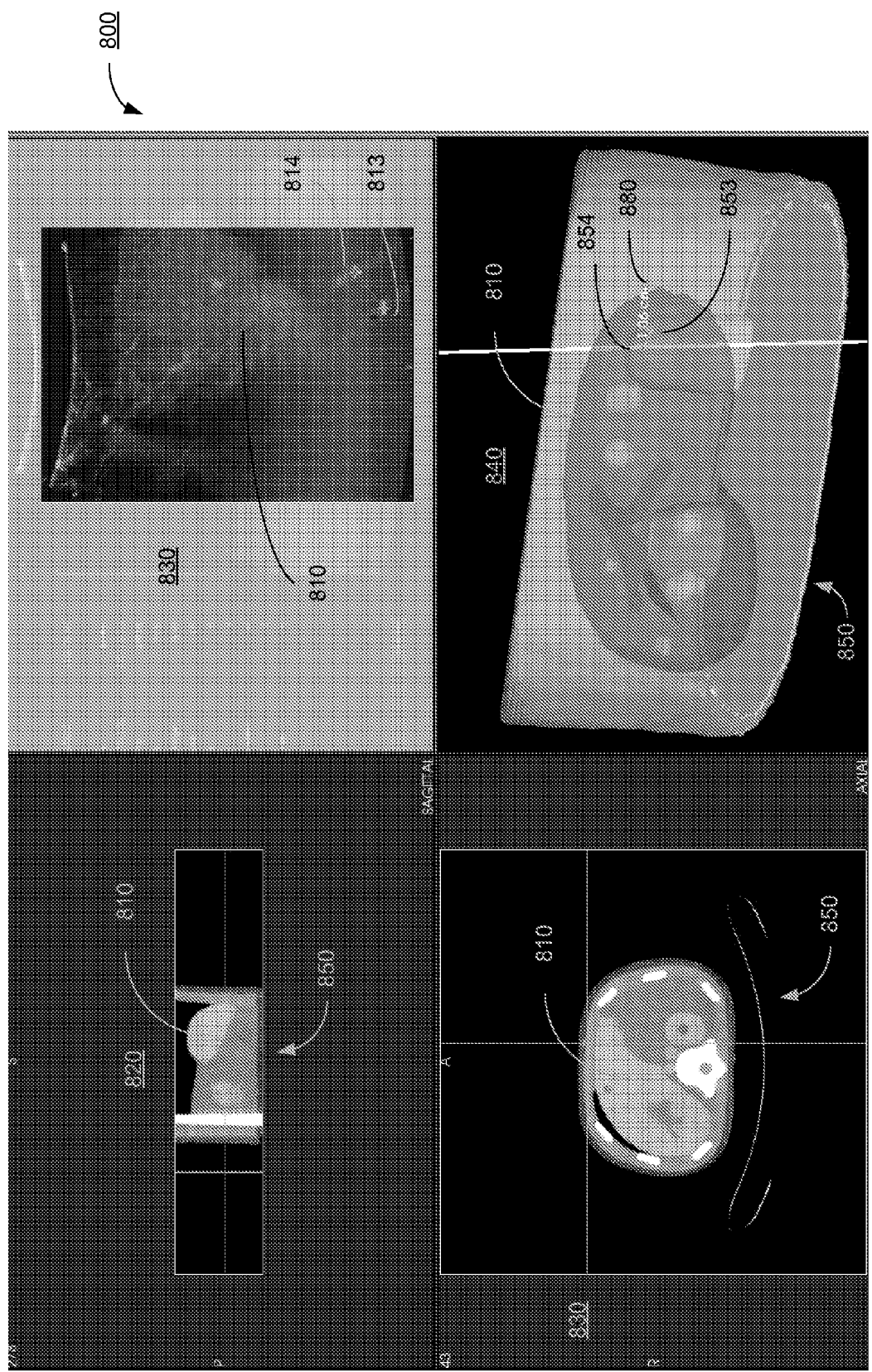
FIG. 8 is a user interface for an image-guided surgery, according to an embodiment.

FIG. 8 depicts a display 800 available to a surgeon during an IGT procedure. The display 800 can be displayed on, for example, the display 111, as shown and described above with reference to FIG. 1. As shown, the display includes a sagittal view 820 of a model 850 of a patient's liver 810, an axial view 830 of the model 850 of the liver 810, a 3D view 840 of the model 850 of the liver 810, and an ultrasound image 830 of the liver 810. The ultrasound image 830 includes an image of a first surgical instrument 813 and an image of a second surgical instrument 814. The first surgical instrument 813 has been transformed onto the model 850 and a rendering of the first surgical instrument 853 is displayed. Similarly, a rendering of the second surgical instrument 854 is displayed in the 3D view 840. Based on the transformation of the surgical instruments to the model, a distance 880 between the first surgical instrument 813, 853, and the second surgical instrument 814, 854 is shown. The distance 880 can be calculated in 3D space. The distance 880 can be more accurate than a 2D distance (e.g., the 2D distance 680 shown and described above with reference to FIG. 6). For example, in an embodiment where a distance vector defined by the tip of the first instrument 813 and the tip of the second instrument 814 has a component that is not coplanar with a 2D image (also referred to as a "non-coplanar component"), a 2D ultrasound distance may be less accurate than the 3D distance 880.

While the methods and systems described above refer to matching an intra-operative surface of any suitable organ to a corresponding preoperative image, in some embodiments, the systems and methods described herein can be used to match an intraoperative surface of the skin of a patient to a preoperative image (e.g., from a CT scan, MRI, or the like). For example, in some instances, a portion of the abdomen can be scanned prior to an interventional procedure and a surface of the skin of the abdomen can be used to register anatomical features in physical space to the corresponding features in the preoperative scan.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

While various embodiments have been described above, it should be understood that they have been presented by way of example only, and not limitation. For example, although various embodiments are described herein as including ablation instruments 113, 114, in other embodiments, any suitable medical instrument can be used (e.g., a probing instrument). In another example, although the system 100 has been illustrated and described herein as including an optical tracking system 115, in some embodiments, the system can include an electromagnetic tracking system. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. Similarly, where methods and/or events described above indicate certain events and/or procedures occurring in certain order, the ordering of certain events and/or procedures may be modified. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above. For example, although some embodiments are described as having two surgical instrument, in some embodiments, there maybe only one surgical instrument. In another example, in some embodiments, the system, apparatus, and/or methods described herein are configured to localize and/or determine the relative position of three, four or more surgical instruments.

What is claimed is:

1. A method comprising:
capturing a first intra-operative 2-D ultrasound image depicting at least a portion of a first flexible surgical needle instrument disposed at a first position with respect to a target tissue of a patient and not a second flexible surgical needle instrument disposed at a second position with respect to the target tissue of the patient, wherein the second position is different from the first position and the first and second flexible surgical needle instruments are concurrently present respectively at the first and second positions when the first intra-operative 2-D ultrasound image is captured;
capturing a second intra-operative 2-D ultrasound image depicting at least a portion of the second flexible surgical needle instrument disposed at the second position with respect to the target tissue of the patient and not the first flexible surgical needle instrument disposed at the first position with respect to the target tissue of the patient, wherein the first and second surgical instruments are concurrently present respectively at the first and second positions when the second intra-operative 2-D ultrasound image is captured, wherein the first and second flexible surgical needle instruments are sequentially manually positioned at the first and second positions;
transforming each of the first and second intra-operative 2-D ultrasound images to a three-dimensional model such that (1) the first position of the portion of the first flexible surgical needle instrument is rendered with the three-dimensional model, and (2) the second position of the portion of the second flexible surgical needle instrument is rendered with the three dimensional model by registering the first intra-operative 2-D ultrasound image to the 3-D model and registering the second intra-operative 2-D ultrasound image to the 3-D model, wherein the 3-D model is generated based on a pre-operative image of the target tissue of the patient acquired before the first flexible surgical needle instrument is disposed at the first position with respect to the target tissue of the patient;
calculating a three-dimensional distance between the portion of the first flexible surgical needle instrument and the portion of the second flexible surgical needle instrument based on the three-dimensional model; and
determining a size of an irreversible electroporation zone from the three-dimensional distance between the portion of the first flexible surgical needle instrument and the portion of the second flexible surgical needle instrument.

2. The method of claim 1, wherein the first flexible surgical needle instrument is a first ablation needle, the second flexible surgical needle instrument is a second ablation needle.

3. The method of claim 1, further comprising:
obtaining a diagnostic image of at least a portion of the patient prior to the first surgical instrument being disposed in the first position; and
generating the three-dimensional model based, at least in part, on the diagnostic image.

4. The method of claim 1, further comprising:
capturing the pre-operative image of the target tissue of the patient prior to the first flexible surgical needle instrument being disposed in the first position;
generating the three-dimensional model based, at least in part, on the pre-operative image; and
registering the first and second intra-operative 2-D ultrasound images to the three-dimensional model.

5. The method of claim 1, further comprising:
capturing a first pre-operative image of the target tissue of the patient prior to the first flexible surgical needle instrument being disposed in the first position;
generating the three-dimensional model based, at least in part, on the first pre-operative image;
capturing a second pre-operative image of the target tissue of the patient after the first pre-operative image is captured and before the first flexible surgical needle instrument is disposed in the first position; and
registering the second pre-operative image to the three-dimensional model, wherein the transforming the first and second intra-operative 2-D ultrasound images is based, at least in part, on the registration of the second pre-operative image to the three-dimensional model.

6. The method of claim 1, wherein a distance vector defined by a tip of the first flexible surgical needle instrument and a tip of the second flexible surgical needle instrument has a non-coplanar component with respect to the first and second intra-operative 2-D ultrasound images.

7. The method of claim 1, further comprising:
generating the three-dimensional model based, at least in part, on a computed tomography scan of at least a portion of the patient including the target tissue, the computed tomography scan being performed before the first flexible surgical needle instrument is disposed in the first position; and capturing a pre-operative ultrasound image of the portion of the patient including the target tissue before the first flexible surgical needle instrument is disposed in the first position.

8. The method of claim 1, further comprising:

generating the three-dimensional model based, at least in part, on a computed tomography scan of at least a portion of the patient including the target tissue, the computed tomography scan being performed before the first flexible surgical needle instrument is disposed in the first position;

capturing a pre-operative ultrasound image of the portion of the patient before the first flexible surgical needle instrument is disposed in the first position; and registering the pre-operative ultrasound image to the three-dimensional model before the first surgical instrument is disposed in the first position.

9. The method of claim 8, wherein the first and second flexible surgical needle instruments include infrared light emitting diodes, and further comprising:

an infrared tracking device that includes lenses that receive light from the infrared light emitting diodes, wherein the registering is based on the received light, and wherein the transforming is based on the registration.

10. A system, comprising:

a first surgical instrument, wherein the first surgical instrument includes a first flexible ablation needle;

a second surgical instrument, wherein the second surgical instrument includes a second flexible ablation needle;

an ultrasound imaging device configured to capture a first intra-operative 2-D ultrasound image of at least a portion of the first surgical instrument disposed with respect to a target tissue of a body of a patient and a second intra-operative 2-D ultrasound image of a portion of the second surgical instrument disposed with respect to the target tissue of the body of the patient, wherein the first instrument is absent in the second intra-operative 2-D ultrasound image, and the second instrument is absent in the first intra-operative 2-D ultrasound image, and the first and second instruments are concurrently present with respect to the target tissue of the body of the patient, wherein the first and second surgical instruments are sequentially manually positioned at the first and second positions; and a processing device configured to transform the first and second intra-operative 2-D ultrasound images to a three-dimensional model of at least a portion of the patient including the target tissue by registering the first intra-operative 2-D ultrasound image to the 3-D model and registering the second intra-operative 2-D ultrasound image to the 3-D model, wherein the 3-D model is generated based on a pre-operative image of the target tissue of the patient acquired before the first surgical instrument is disposed at the first position with respect to the target tissue of the patient, the processing device configured to calculate a distance, in model space, between at least a portion of the first surgical instrument and at least a portion of the second surgical instrument based, at least in part, on the three-dimensional model, the distance in model space correlating to a three-dimensional distance in physical space between the portion of the first surgical instrument and the portion of the second surgical instrument, wherein the processor determines a size of an irreversible electroporation zone from the three-dimensional distance.

11. The system of claim 10, wherein the ultrasound imaging device is configured to capture an ultrasound image of at least a portion of the patient including the target tissue, the ultrasound image not including the first surgical instrument or the second surgical instrument, the processing device is configured to register the ultrasound image to the three-dimensional model before the first intra-operative 2-D ultrasound image is captured.

12. The system of claim 10, wherein: the three-dimensional model is generated using computed tomography, the processing device is configured to transform the first and second intra-operative 2-D ultrasound images to the three-dimensional model.

13. The system of claim 10, wherein the ultrasound imaging device is configured to capture a third intra-operative ultrasound image of at least a portion of the patient including the target tissue, the third intra-operative ultrasound image not including the first surgical instrument or the second surgical instrument, and the processing device is configured to register the third intra-operative ultrasound image to the three-dimensional model, wherein the three-dimensional model is generated intra-operative.

14. The system of claim 10, wherein: the processing device is configured to calculate the distance between the portion of the first surgical instrument and the portion of the second surgical instrument intra-operatively.

15. A non-transitory processor-readable medium storing code representing instructions to be executed by a processor, the code comprising code to cause the processor to:

render a three-dimensional model of at least a portion of a patient including a target tissue;

receive a first intra-operative 2-D ultrasound image of a first surgical instrument and a second intra-operative 2-D ultrasound image of a second surgical instrument, wherein the first and second surgical instruments respectively include a first flexible monopolar electroporation probe and a second flexible monopolar electroporation probe, which are sequentially manually positioned with respect to the target tissue of the patient and concurrently at least partially visible in the first and second intra-operative 2-D ultrasound images;

transform the first and the second intra-operative 2-D ultrasound images to the three-dimensional model by registering the first intra-operative 2-D ultrasound image to the 3-D model and registering the second intra-operative 2-D ultrasound image to the 3-D model, wherein the 3-D model is generated based on a pre-operative image of the target tissue of the patient acquired before the first surgical instrument is disposed at the first position with respect to the target tissue of the patient;

calculate a 3-D distance between a portion of the first surgical instrument and a portion of the second surgical instrument based on the 3-D model; and determine a size of an irreversible electroporation zone from the 3-D distance between the portion of the first surgical instrument and the portion of the second surgical instrument, which is determined based, at least in part, on the transformation of the first and second intra-operative 2-D ultrasound images to the three-dimensional model.

16. The non-transitory processor-readable medium of claim 15, wherein the three-dimensional-model is generated from a pre-operative image of at least a portion of the patient including the target tissue.

17. The non-transitory processor-readable medium of claim 15, wherein the imaging device is an ultrasound imaging device.

18. The non-transitory processor-readable medium of claim 15, the code further comprising code to cause the processor to:
receive a reference image of at least a portion of the patient including the target tissue; and
register the three-dimensional model to the patient based, at least in part, on the reference image.

19. The non-transitory processor-readable medium of claim 15, the code further comprising code to cause the processor to:
receive, before the first and second intra-operative 2-D ultrasound images are received, a reference image of at least a portion of the patient including the target tissue; and
register the three-dimensional model to a physical space associated with the patient based, at least in part, on the reference image.

\* \* \* \* \*